United States Patent [19]

Speiser et al.

[11] Patent Number: 5,424,332

[45] Date of Patent: * Jun. 13, 1995

[54] PHARMACEUTICAL COMPOSITION AND PROCESS FOR THE PRODUCTION THEREOF

[76] Inventors: Peter P. Speiser, Freudenbergstrasse 101/D2, 8044 Zürich; Rajendra K. Joshi, Alstetterstrasse 224, 8048 Zürich, both of Switzerland

[*] Notice: The portion of the term of this patent subsequent to Sep. 25, 2007 has been disclaimed.

[21] Appl. No.: 114,689

[22] Filed: Aug. 31, 1993

Related U.S. Application Data

[60] Continuation-in-part of Ser. No. 881,479, May 11, 1992, abandoned, which is a continuation-in-part of Ser. No. 582,237, Sep. 14, 1990, abandoned, which is a division of Ser. No. 109,780, Oct. 19, 1987, Pat. No. 4,959,389.

[51] Int. Cl.6 .................... A01N 55/02; A61K 31/315
[52] U.S. Cl. .................... 514/547; 514/494; 514/502; 514/825; 514/863
[58] Field of Search ............ 514/547, 494, 502, 825, 514/863

U.S. PATENT DOCUMENTS 4,851,439  7/89  Speiser et al. ............ 514/547
4,959,389  9/90  Speiser et al. ............ 514/494

FOREIGN PATENT DOCUMENTS 2621214  11/77  Denmark .
0188749  12/85  European Pat. Off. .
1426959  12/65  France .
2530372  1/77  Denmark .

OTHER PUBLICATIONS

Gopher and Gutman, FESB letters, 67, 130 (1976)
Chemical Abstracts 105:190496y (1986)
Chemical Abstracts 86:96018m (1977)
Chemical Abstracts 92:11228f (1979)
Bayard et al., Der Hautarzt, (1987), 38:279-285
Schweckendiek "Fumarsäure bei Psoeiasis eine neue Enttamschung (1980)
Niebuer et al., J. Am. Acad. Derm. 20(4)1601 (April 1989)
Roenick et al., Ed. "Psoriasis", *Dermatology*, 5, Marcel Dekker, (1985)
Skoven et al., Arch. Derm. 115, 1185-1187 (1979)
Heng, Br. J. Dermatology, 106, 107 (1982)
M. Gordon et al., Arch. Derm. 95:402-407, (April 1967)
Neumann et al., J. Derm., 79:3, 160 (1968)

*Primary Examiner*—Raymond Henley, III
*Assistant Examiner*—Keith MacMillan
*Attorney, Agent, or Firm*—Cohen, Pontani, Lieberman, Pavane

[57] ABSTRACT

A pharmaceutical composition in dosage form for treating psoriasis and psoriatic arthritis includes, essentailly, as active substance (s), a fumaric acid monoalkylester salt having the formula

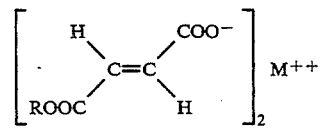

wherein R is a methyl, propyl or isopropyl group, and $M^{++}$ is calcium, alone or in combination with at least one of the fumaric acid alkyl ester salts as defined above, $M^{++}$ is selected from the group consisting of magnesium, zinc and iron. The combination includes, by weight, 10–250 parts, 0–50 parts magnesium, and 0–50 parts zinc or iron salt of fumaric acid monoalkylester, in an amount of fumaric acid not exceeding 300 mg. per dosage form, in combination with ordinary pharmaceutically compatible solid adjuvants and vehicles.

11 Claims, No Drawings

PHARMACEUTICAL COMPOSITION AND PROCESS FOR THE PRODUCTION THEREOF

RELATED APPLICATIONS

This application is a continuation-in-part of U.S. patent application Ser. No. 07/881,479, filed May 11, 1992, now abandoned which was a continuation-in-part of U.S. patent application Ser. No. 07/582,237 filed Sep. 14, 1990, now abandoned which was a divisional of U.S. patent application Ser. No. 07/109,780 filed Oct. 19, 1987 and issued as U.S. Pat. No. 4,959,389.

FIELD OF THE INVENTION

The present invention relates to pharmaceutical preparations for the treatment of psoriasis and psoriatic arthritis as well as to the use of these preparations as systemic therapy for the treatment of these diseases.

BACKGROUND ART

Pharmaceutical preparations which after administration enter, upon their biological degradation, into the citric acid cycle or belong to it are acquiring greater and greater therapeutic valve, generally in high doses, since it is possible to mitigate or cure cryptogenically induced diseases with them.

Thus, fumaric acid impedes the growth of the Ehrlich ascites tumor in mice, reduces the toxic effects of mitomycin C and aflotoxin (K. Kuroda, M. Akao, Biochem, Pharmacol. 29, 2839–2844 (1980)/Gann. 72, 77–782 (1981)/Cancer Res. 36. 1900–1903 (1976)) and has an anti-psoriatic as well as antimicrobic action (C. N. Huhtsnen, J. Food Sci. 48, 1574 (1983)/M. N. Islam, U.S. Pat. No. 4,346,118 issued Aug. 24, 1982/C.A. 97, 161317b (1982)).

High doses of umaric acid or its presently known derivatives such as dihydroxy fumaric acid, fumaramide and fumaronitrile have such an unacceptable rate of adverse effects and high toxicity upon parenteral, dermal and, in particular, peroral adminstration (P. Holland, R. G. White, Brit, J. Dermatol. 85, 259–263 (1971)/M. Hadedorn, K. W. Kalkoff, G. Kiefer, D. Baron, J. Hug, J. Petres, Arch. Derm. Res. 254, 67–73 (1975)), that up to now it has been necessary in most cases to refrain from such therapy.

In European Patent Application No. 85 116 011.9 of Dec. 16, 1985, fumaric acid derivatives and pharmaceutical preparations containing them have already been described for the treatment of psoriasis.

SUMMARY OF THE INVENTION

It has now been surprisingly found that an in general considerably improved action can be obtained from combination preparations which contain one or more compounds from the group of calcium, magnesium, zinc and iron salts of fumaric acid monoalkyl ester of the general formula

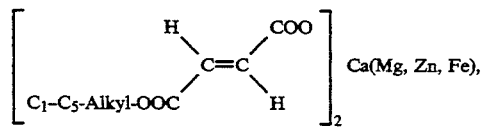

alone or preferably in combination with dialkyl fumarate of the formula

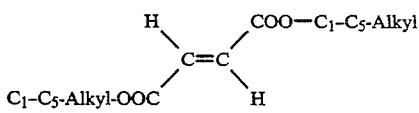

and ordinary pharmaceutical compatible adjuvants and vehicles. $C_1$-$C_5$ alkyl groups include straight-chain and branched-chain alkyl groups, particularly a methyl, propyl or isopropyl group.

PRESENTLY PREFERRED EMBODIMENTS

A particularly preferred pharmaceutical composition in dosage form for the treatment of psoriasis and psoriatic arthritis consists, as active substance(s), essentially of a fumaric acid monoalkylester salt having the formula

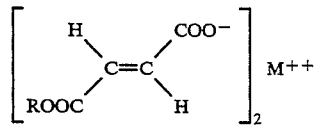

where in R is a methyl, propyl or isopropyl group, and $M^{++}$ is calcium, alone or in combination with at least one of said fumaric acid alkyl ester salts as defined above wherein $M^{++}$ is selected from the group consisting of magnesium, zinc and iron said combination comprising 10–250 parts by weight of said calcium, 0–50 parts by weight of said magnesium, and 0–50 parts by weight of said zinc or iron salt of fumaric acid monoalkylester, in an amount of fumaric acid not exceeding 300 mg. per dosage form, in combination with ordinary pharmeceutically compatible solid adjuvants and vehicles. More preferably the active substance consists essentially of fumaric acid monomethyl ester calcium salt. The active substances may also consist essentially or a combination of furamic acid monomethyl ester calcium salt, fumaric acid monomethyl ester zinc salt and fumaric acid monomethyl ester magnesium salt, of a combination of fumaric acid monomethyl ester calcium salt, fumaric acid monomethyl ester zinc salt and fumaric acid monomethyl ester iron salt, of fumaric acid monomethyl ester calcium salt in combination with fumaric acid monomethyl ester iron salt, of fumaric acid monopropyl ester calcium salt, of fumaric acid monopropyl ester calcium salt in combination with fumaric acid monomethyl ester zinc salt and fumaric acid monomethyl ester magnesium salt, of a combination of fumaric acid monopropyl ester calcium salt, fumaric acid monomethyl ester zinc salt and fumaric acid monomethyl ester iron salt or of fumaric acid monopropyl ester calcium salt in combination with fumaric acid monomethyl ester iron salt. Preferably, the pharmaceutical composition is prepared in the form of a capsule, granulate or tablet in the form of an ointment, plaster, lotion or as parenteral solution.

Preferred combination preparations in accordance with the invention contain the calcium salt of fumaric acid monoethylester, the calcium salt of fumaric acid monoethylester combined with dimethylfumarate, the calcium and zinc salts of fumaric acid monomethylester combined with dimethylfumarate, or the calcium, magnesium and zinc salts of fumaric acid monoethylester in combination with dimethylfumarate.

For oral administration, combination preparations which contain the calcium salt of fumaric acid monoalkylester in an amount of 100 to 300 mg are particularly suitable, the total weight of the active substances being 100 to 300 mg.

Other perferred oral forms of administration contain 10 to 290 parts by weight of the calcium salt of fumaric acid monoalkylester and 290 to 10 parts by weight of dimethylfumarate, 10 to 250 parts by weight of the calcium salt of fumaric acid monoalkylester, 1 to 50 parts by weight of dimethylfumarate and 1 to 50 parts by weight of the zinc salt of fumaric acid monoalkylester or 10 to 250 parts by weight of the calcium salt of fumaric acid monoalkylester, 250 to 10 parts by weight of dimethylfumarate, 1 to 50 parts by weight of the magnesium salt of fumaric acid monoalkylester and 1 to 50 parts by weight of the zinc salt of fumaric acid monoalkylester, the total weight of the active substances being 100 to 300 mg in each case.

For systemic initiation of the treatment or conclusion thereof a low dose is advantageous, containing, for instance, 30.0 mg dimethylfumarate, 67.0 mg of the calcium salt of monoethylfumarate, 5.0 mg. of the magnesium salt of monoethylfumarate and 3.0 mg of the zinc salt of monoethylfumarate.

For the therapeutic dose after the initiating phase there can be used, for instance, a dose of 120.0 mg dimethylfumarate, 87.0 mg of the calcium salt of monoethylfumarate, 5.0 mg of the magnesium salt of monoethylfumarate and 3.0 mg of the zinc salt of monoethylfumarate.

The fumaric acid derivatives contained in the preparations of the invention are obtained, for instance, in the manner that a compound of the formula

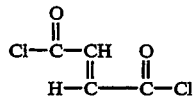

a) is condensed with 2 mols of alkyl alcohol (ROH) to form the diester and then hydrolyzed in controlled fashion to form the monoester, or
b) condensed with 1 mol of a corresponding alkyl alcohol (ROH) whereupon the monoacid chloride obtained is hydrolyzed to the acid, or
c) fumaric acid is condensed directly with 2 mols of alkyl alcohol (ROH) to form a diester and then hydrolyzed under controlled conditions to the monoester, or
d) maleic acid or maleic anhydride is condensed directly with 1 to 2 mols of the corresponding alkyl alcohol (ROH) to form a mono- or diester and then catalytically isomerized to form the corresponding fumaric acid ester.

The salts of the fumaric acid monoalkylesters can be obtained by reacting a compound of the general formula

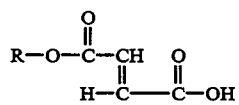

in which R is a $C_1$–$C_5$ alkyl group, with one-half mol of Ca, Mg or Zn hydroxide or oxide in toluene and azeotropically removing the water which has formed during the reaction.

EXAMPLE 1

Preparation of enteric-coated film tablets containing 210 mg of monoethylfumarate Ca salt corresponding to 150 mg of fumaric acid 21.000 kg of monoethylfumarate calcium salt are crushed, mixed and homogenized by means of an 800 screen applying suitable precautionary measures (breathing mask, gloves, protective clothing, etc.). A mixture of adjuvants having the following composition is then prepared: 20.000 kg of starch derivative (STA-RX 1500 ®), 2.000 kg of microcrystalline cellulose (Avicel PH 101 ®), 0.600 kg of polyvinyl pyrrolidone (PVP, Kollidon ®25), 4.000 kg Primogel ®, 0.300 kg of colloidal silicic acid (Arosil ®). The total powder mixture is treated with the active substance, homogenized by means of a 200 screen and worked with a 2% aqueous solution of polyvinyl pyrrolidone (Kollidon ® K 30) in customary manner to form a binder granulate and then mixed in dry state with the outer phase. The latter consists of 2.000 kg of a so-called FST complex, containing 80% talc, 10% silicic acid and 10% magnesium stearate. It is then pressed in customary manner to form barreled tablets of a weight of 500 mg and a diameter of 11.5 mm. Instead of these conventional methods of tabletting, other methods for the production of tablets can also be used, such as direct tabletting as well as solid dispersions by the melt method and the spray-drying method.

Enteric Coating

A solution of 2.250 kg of hydroxy propylmethyl cellulose phthalate (HPMCP, Pharmacoat HP 50 ®), is dissolved in a solvent mixture of 2.50 liters of demineralized water, 13.00 liters of acetone Ph. Helv. H VII and 13.00 liters of ethanol 94 wt % and the solution is treated with 2.40 kg of castor oil (European Pharmacopoeia II). The solution is gelled in a coating kettle in traditional manner in separate portions on the tablet cores or sprayed thereon or applied in a fluidized bed-like apparatus.

After suitable drying, the film coating is then applied. It consists of a solution of Eudragit ® E 12.5%, 4.800 kg, colored lacquer ZLT 2 blue (Siegle) 0.210 kg, titanium (VI)-oxide Kronos RN 56, 0.520 kg, talc (European Pharmacopoeia) 0.340 kg and polyethylene glycol 6000 Ph. Helv. VII 0.120 kg, in a solvent mixture of 8.200 kg 2-propanol, Ph. Helv. VII, 0.060 kg glycerine triacetate and 0.200 kg demineralized water.

After homogenous distribution in the coating kettle or fluidized bed, drying is effected, followed by polishing in the customary manner.

EXAMPLE 2

Production of enteric-coated capsules containing 86.5 mg of monoethylfumarate Ca salt and 110.0 mg of dimethylfumarate corresponding to a total of 150 mg of fumaric acid 8.650 mg of monoethylfumarate Ca salt and 11.000 kg of dimethylfumarate are mixed intensively with a mixture consisting of 15.000 kg starch, 6.000 kg lactose Ph. Helv. VII, 2.000 kg microcrystalline cellulose (Avicel ®), 1.000 kg polyvinyl pyrrolidone (Kollidon ® 25) and 4.000 kg Primogel ® and homogenized by means of an 800 screen, applying suitable precautionary measures (breathing mask, gloves, protective clothing, etc.). The entire powder mixture is worked with a 2% aqueous solution of polyvinylpyrrolidone (Kollidon ® 25) in customary manner to form a binder granulate and mixed in dry state with the outer phase. The latter consists of 0.350 kg of colloidal silicic acid (Aerosil ®), 0.500 kg of Mg stearate and 1.500 kg of talc Ph. Helv. VII. The homogeneous mixture is then filled into suitable hard-gelatine capsules in portions of 500.0 mg which are finally provided in customary manner with an enteric coating consisting of hydroxypropyl methylcellulose stearate and castor oil as softener. Instead of effecting the filling into hard gelatine capsules it can be effected into corresponding enteric-coated capsules consisting of a mixture of cellulose acetate phthalate (CAP) and hydroxypropyl ethyl cellulose phthalate (HPMCP).

EXAMPLE 3

Production of enteric-coated capsules containing 203.0 mg of monoethylfumarate Ca salt as well as 5.0 mg of monoethylfumarate Mg salt and 3.0 mg of monoethylfumarate Zn salt corresponding to a total of 150 mg of fumaric acid 20.300 kg of monoethylfumarate Ca salt as well as 0.500 kg of monoethylfumarate Mg salt and 0.300 kg of monoethylfumarate Zn salt are crushed, mixed intensively and homogenized by means of an 800 screen taking suitable precautionary measures (breathing mask, gloves, protective clothing, etc.) To this mixture of active substances, there is added a homogeneous powder mixture of the following composition: spray-dried lactose 12.900 kg, colloidal silicic acid 1.000 kg, microcrystalline celluose (Avicel ®) 2.000 kg, magnesium stearate (Ph. Helv. VII) 1.000 kg and talc (PH. Helv. VII) 2.000 kg. The entire powder mixture is homogenized again by means of a 200 screen and then filled into two-piece hard gelatine capsules of a net weight of 400 mg enclosed. The coating with an enteric coating is effected in the same way as in Example 2.

EXAMPLE 4

Production of enteric-coated tablets containing 87.0 mg monoethylfumarate Ca salt, 120.0 mg dimethylfumarate, 5.0 mg monoethylfumarate Mg salt and 3.0 mg monoethylfumarate Zn salt corresponding to 164 mg fumaric acid ("Forte" tablets)

12.000 kg fumaric acid dimethylester, 8.700 mg monoethylfumarate Ca salt, 0.500 kg monoethylfumarate Mg salt and 0.300 kg monoethyl fumarate Zn salt are crushed, mixed intensively and homogenized by means of an 800 screen, observing suitable precautionary measures (breathing mask, gloves, protective clothing, etc.). An adjuvant mixture of the following composition is prepared in a manner similar to that described under Example 1, namely starch derivative (STA-RX 1500 ®) 18.000 kg, microcrystalline cellulose (Avicel pH 101 ®) 0.300 kg, polyvinyl pyrrolidone (PVP, Kollidon ®120) 0.750 kg, Primogel ® 4.000 kg, and colloidal silicic acid (Aerosil ®) 0.250 kg.

Adjuvants and the combination of active substances are vigorously mixed and homogenized by means of a 200 screen. The entire mixture is worked together with a 2% aqueous solution of polyvinyl pyrrolidone (Kollidon ®K25) in the customary manner to form a binder granulate and mixed in dried state with the outer phase. The latter consists of 0.500 kg Mg stearate (Ph. Eur.) and 1.500 kg talc (Ph. Eur. II). The entire granulate is then compacted in customary manner to form barreled tablets of 500 mg gross weight and 11.5 mm in diameter.

Instead of this conventional tabletting method other methods for the production of tablets can also be used, such as direct tabletting and solid dispersions by the melting and spary-drying method.

The enteric coating can be applied in a conventional coating kettle or sprayed on or be applied in a fluidized bed apparatus. For resistance to the gastric juice a solution of 2.250 kg hydroxypropyl methyl cellulose phthalate (HPMCP, Pharmacoat HP 50 ®) is dissolved in portions in a mixture of the following solvents: acetone 13.00 liters, ethanol 94 weight % denatured with 2% ketone 13.50 liters, and demineralized water 2.50 liters. Castor oil Ph Eur. 0.240 kg is added as softener to the final solution and the solution is applied in customary manner in separate portions to the barreled tablet cores.

Film coating: After the drying a suspension of the following composition is then applied as film coating in the same apparatus: talc Ph Eur II 0.340 kg, titanium (VI) oxide Cronus Rn 56 ® 0.400 kg, colored lacquer L-red lacquer 85237N 0.324 kg, Eudragit E. 12.5% ® 4.800 kg and polyethylene glycol 6000 pH 11 XI 0.120 kg in a solvent mixture of the following composition: 2-propanol DAB 8.170 kg, demineralized water 0.200 kg and glycerine triacetate (Triacetine ®) 0.060 kg.

EXAMPLE 5

Preparation of enteric-coated film tablets containing 67.0 mg monoethylfumarate Ca salt, 30.0 mg dimethylfumarate, 5.0 mg monoethylfumarate Mg salt and 3.0 mg monoethylfumarate Zn salt corresponding to 75 mg fumaric acid ("mite" tablets)

3.000 kg fumaric acid dimethylester, 6.700 kg monoethylfumarate Ca salt, 0.500 kg monethylfumarate Mg salt as well as 0.300 kg monoethylfumarate Zn salt are crushed, mixed intensively and homogenized by means of an 800 screen. In this connection suitable protective measures should be taken such as breathing mask, gloves, protective clothing, etc. It is then added to a mixture consisting of 30.000 kg starch derivative (STA-RX 1500 ®), 3,000 kg microcrystalline cellulose (Avicel pH 101 ®), 0.750 k polyvinyl pyrrolidone (PVP Kollidon ®25), 4.000 kg Primogel ®, 0.250 kg colloidal silica (Aerosil ®). The mixture of active substances is mixed until homogeneous, passed through a 200 screen and worked up with a 2% aqueous solution of polyvinyl pyrrolidone (K 25) in customary manner to form a binder granulate. A powder mixture consisting of the following adjuvants is added as outer phase to the dried granulate: 0.500 kg Mg stearate Ph. Eur. II and 0.800 kg talc Ph. Helv. VII.

The homogenous granulate mixture is compacted in customary manner to form barreled tablet cores of a weight of 500.00 mg and a diameter of 11.5 mm. In addition to the binder methods other tabletting methods can also be used, in accordance with Examples 1 and 4.

The coating of the tablet cores with an enteric coating and with a film coating is effected in a manner similar to that described under Examples 1 and 4.

The preparations in accordance with the invention are preferable administered orally in the form of tablets or capsules. These solid single-dose forms being preferably provided with an enteric coating which, after passage through the stomach, dissolves in the juice of the small-intestine within a few minutes and liberates the active principle from the preparation. For the systemic initiation or termination a low dose ("mite") is necessary; for the therapeutic dose after the initiation phase a higher dose ("forte") is necessary.

It has been found that the mixed preparations of the invention exhibit upon oral adminstration a considerably better action against the different clinical forms of psoriasis and psoriatic arthritis.

Since the activity of phospholipase $A_2$ is changed in a psoriatic epidermis, a possible explanation of the mechanism of action of the combination preparations of the invention lies in this enzyme being stimulated by calcium monoethylfumarate, whereas Mg and Zn cations are of great importance for the skin metabolism of psoriasis patients.

An object of the invention, in addition to orally administrable preparations in the form of capsules, granulates and tablets, is preparations for cutaneous and transdermal adminstration in the form of ointments, plasters, lotions and douche agents, for parenteral adminstration in the form of aqueous microdispersions, O/W emulsions or oily solutions, for rectal administration as suppositories or micro-enemas and for the medicinal treatment of hair, fingernails and toenails.

Therapeutic treatment with the composition according to example 4 and the results thereof In an intra-individual case-control study over a period of a year the ambulant peroral treatment of psoriasis was observed on a total of 24 patients (see Table 1). All 25 patents had previously responded poorly to conventional medicines and forms of therapy, so that it can be termed a negative selection.

Half of all the ambulant perorally treated patents showed substantial improvement objectively, this improvement generally taking place only after treatment for several weeks.

No severe objective adverse effects were noted, in particular disturbances of kideny or liver function or changes in blood count.

The acute toxicity was studed orally on mice and rats before the clinical trial. The results showed very low toxicity of the fumaric acid derivatives used (see Table 2).

TABLE 1

| | Clinical Results | |
|---|---|---|
| | Study I<br>n = 13 patients<br>formulation<br>according to<br>Example 4 | Study II<br>n = 11 patients<br>formulation<br>according to<br>Example 4 |
| 1. Duration of the treatment | 3 months | 1 year |
| 2. Results: | | |
| very good | 4 patients | 5 patients |
| good | 3 patients | 1 patient |
| unsatisfactory | 4 patients | 3 patients |
| 3. Discontinuation of therapy because of adverse effects | 2 patients | 2 patients |

TABLE 2

| Acute Toxicity Study (peroral) | | | |
|---|---|---|---|
| | Sex of Animals | Composition according to Example 4 | |
| | | Mice | Rats |
| $LD_{50}$ (24 hours) in mg/kg | male | 5750 | 4700 |
| | female | 8200 | 4600 |
| $LD_{50}$ (14 days) in mg/kg | male | 5600 | 4700 |
| | female | 6950 | 3900 |
| Lowest Toxical Dose in mg/kg | male | 3160 | 3160 |
| | female | 3160 | 3160 |
| Lowest Lethal Dose in mg/kg | | 5620 | 4640 |
| Stomach & Intestinal Wall Haemorragic in | | 5600 | none |

TABLE 2-continued

| Acute Toxicity Study (peroral) | | | |
|---|---|---|---|
| | Sex of Animals | Composition according to Example 4 | |
| | | Mice | Rats |
| mg/kg | | | |
| Spleen Inflammatory | | none | none |
| Oedema Epithelial | | none | none |

What is claimed is:

1. A pharmaceutical composition in dosage form for the treatment of psoriasis and psoriatic arthritis consisting, as active substance(s), essentially of a fumaric acid monoalkylester salt having the formula

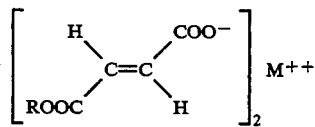

wherein R is a methyl, propyl or isopropyl group, and $M^{++}$ is calcium, alone or in combination with at least one of said fumaric acid alkyl ester salts as defined above wherein $M^{++}$ is selected from the group consisting of magnesium, zinc and iron said combination comprising 10-250 parts by weight of said calcium, 0-50 parts by weight of said magnesium, and 0-50 parts by weight of said zinc or iron salt of fumaric acid monoalkylester, in an amount of fumaric acid not exceeding 300 mg. per dosage form, in combination with ordinary pharmaceutically compatible solid adjuvants and vehicles.

2. The pharmaceutical composition according to claim 1, wherein the active substance consists essentially of fumaric acid monomethyl ester calcium salt.

3. The pharmaceutical composition according to claim 1, wherein the active substances consist essentially of a combination of fumaric acid monomethyl ester calcium salt, fumaric acid monomethyl ester zinc salt and fumaric acid monomethyl ester magnesium salt.

4. The pharmaceutical composition according to claim 1, wherein the active substances consist essentially of a combination of fumaric acid monomethyl ester calcium salt, fumaric acid monomethyl ester zinc salt and fumaric acid monomethyl ester iron salt.

5. The parmaceutical composition according to claim 1, wherein the active substances consist essentially of fumaric acid monomethyl ester calcium salt in combination with fumaric acid monomethyl ester iron salt.

6. The pharmaceutical composition according to claim 1, wherein the active substance consists essentially of fumaric acid monopropyl ester calcium salt.

7. The pharmaceutical composition according to claim 1, wherein the active substances consist essentially of fumaric acid monopropyl ester calcium salt in combination with fumaric acid monomethyl ester zinc salt and fumaric acid monomethyl ester magnesium salt.

8. The pharmaceutical composition according to claim 1, wherein the active substances consist essentially of a combination of fumaric acid monopropyl ester calcium salt, fumaric acid monomethyl ester zinc salt and fumaric acid monomethyl ester iron salt.

9. The pharmaceutical composition according to claim 1, wherein the active substances consist essentially of fumaric acid monopropyl ester calcium salt in combination with fumaric acid monomethyl ester iron salt.

10. The pharmaceutical composition according to claim 1, in the form of a capsule, granulate or tablet.

11. The pharmaceutical composition according to claim 1, in the form of an ointment, plaster, lotion or as parenteral solution.

* * * * *